(12) United States Patent
Swart et al.

(10) Patent No.: US 7,614,095 B2
(45) Date of Patent: Nov. 10, 2009

(54) AIR BATH WITH BYPASS VENT

(75) Inventors: Peter W. Swart, Oostburg, WI (US); Ronald A. Bauer, Belgium, WI (US); Diana Q. Wang, Sheboygan, WI (US)

(73) Assignee: Kohler Co., Kohler, WI (US)

( * ) Notice: Subject to any disclaimer, the term of this patent is extended or adjusted under 35 U.S.C. 154(b) by 354 days.

(21) Appl. No.: 10/867,539

(22) Filed: Jun. 14, 2004

(65) Prior Publication Data

US 2005/0273922 A1    Dec. 15, 2005

(51) Int. Cl.
*A61H 33/06*    (2006.01)
(52) U.S. Cl. ........................................................ 4/541.5
(58) Field of Classification Search .................. 4/541.1, 4/541.4, 541.5
See application file for complete search history.

(56) References Cited

U.S. PATENT DOCUMENTS

| | | | | |
|---|---|---|---|---|
| 3,086,715 | A | * | 4/1963 | Mineau et al. ................ 4/541.5 |
| 4,325,149 | A | | 4/1982 | Moreland |
| 4,510,967 | A | | 4/1985 | Spinnett et al. |
| 4,628,908 | A | * | 12/1986 | Dupont ........................ 4/541.5 |
| 4,876,753 | A | * | 10/1989 | Bucher ........................ 4/541.5 |
| 4,907,305 | A | | 3/1990 | Teramachi et al. |
| 5,381,563 | A | * | 1/1995 | Isabelle et al. ................ 4/541.5 |
| 5,418,984 | A | | 5/1995 | Livingston, Jr. |
| 5,898,958 | A | | 5/1999 | Hall |
| 5,930,851 | A | | 8/1999 | Brunelle |
| 6,183,430 | B1 | | 2/2001 | Lin |
| 6,185,757 | B1 | | 2/2001 | Gardenier et al. |
| 6,317,903 | B1 | | 11/2001 | Brunelle et al. |
| 6,427,257 | B1 | * | 8/2002 | Castellote .................... 4/541.5 |
| 6,490,740 | B1 | | 12/2002 | Gardenier et al. |
| 6,499,153 | B1 | | 12/2002 | Simoni et al. |
| 6,629,320 | B1 | * | 10/2003 | Gardenier et al. ............ 4/541.5 |
| 2003/0000009 | A1 | | 1/2003 | Brennan et al. |
| 2003/0233704 | A1 | | 12/2003 | Castellote |

FOREIGN PATENT DOCUMENTS

EP    0 744 169 A2    11/1996

* cited by examiner

*Primary Examiner*—Tuan N Nguyen
(74) *Attorney, Agent, or Firm*—Quarles & Brady LLP

(57) ABSTRACT

An air bath has air outlets extending around the side walls of the water basin. Air is delivered to the air outlets through a ring-like air manifold coupled to a blower by conduit. The conduit has a bypass vent that siphons off a portion of the air flow otherwise passing to the air outlets and maintains the blower in communication with ambient air. The air delivery system provides a wider range of bubble densities by allowing the blower to operate at lower speeds without overheating or stalling from back pressure arising from the pressure head of the water in the basin.

17 Claims, 5 Drawing Sheets

AIR BATH WITH BYPASS VENT

CROSS-REFERENCE TO RELATED APPLICATIONS

Not applicable.

STATEMENT OF FEDERALLY SPONSORED RESEARCH OR DEVELOPMENT

Not applicable.

BACKGROUND OF THE INVENTION

The present invention relates to bathtubs in which air is bubbled into the water, and in particular to air delivery systems for such bathtubs.

Therapeutic water baths and pools are well-known. Spas or whirlpool tubs are common examples in which water streams from jets through the walls of the basin flow into the water beneath the surface, usually directed at muscle areas of a person's body, for example shoulders, back and thighs. The force from the jets "massage" the bather directly, as well as agitate the water, to provide therapeutic effects for other parts of the body not directly in the path of the jets. U.S. Pat. No. 6,185,757 discloses one such bath with water jets.

Some tubs instead use air streams to agitate the water. U.S. Pat. Nos. 5,898,958 and 6,317,903 each disclose a tub that introduces air into the water from a blower or air pump passed through conduits and a manifold to air jets in the walls of the tub. The air delivery systems in these patents are rather complex and may require a separate conduit for each air jet.

Co-pending and co-owned U.S. patent application Ser. No. 10/774,123, filed on Feb. 6, 2004, the disclosure of which is hereby incorporated by reference, discloses an air bath with an improved air distribution system that alleviates dead zones (or non-air infused pockets of water in the tub) to more consistently achieve full body treatment. That system helps overcome a problem of the air jets, particularly those farthest from the blower, becoming blocked by the pressure head of the water in the tub, particularly when the blower speed is decreased. The air jets are arranged in rows that extend essentially around the entire perimeter of the basin. The rows of air jets are spaced apart vertically so that the air jets in each row realize a different pressure head, the vertically higher the air jets, the less the pressure head. Thus, when the water level is high and/or the blower is running at a low speed such that the air jets in the lower rows become effectively blocked, air can still flow through the air jets in the higher row(s), thereby maintaining bubbling around the entire perimeter of the basin.

If all the air jets were to become blocked and stay blocked long enough, back pressure could build up sufficient to stall the blower. Heat or current limiting circuitry would have to be provided to shut down the blower motor to keep it from being damaged. A damaged blower motor would render the air system inoperable, and replacement motors are expensive, and typically require a service call from a technician, further adding to the cost. Even if damage to the motor could be avoided, it may still disrupt operation of the bubbling and destroy the air bath.

The system described in the aforementioned patent application helps protect the blower to some extent by keeping open an outlet for the air flow from the blower. However, to avoid even the uppermost air jets from becoming blocked, the blower must be selected and operated at sufficiently high speeds to overcome the pressure head. This somewhat limits the ability to provide soft, low density bubbling, without the use of supplemental tanks or accumulators, as described in U.S. Pat. No. 4,907,305.

U.S. published application 2003/0233704 discloses a bathtub with an air distribution system that can have a pressure relief valve upstream from the air jets to relieve excess pressure from the blower and prevent it from overheating. Thus, this system requires valving that opens in the event of an excess pressure situation to protect the blower motor. And, since this is merely a protective measure, the system does not provide for more subtle bubbling.

Hence, a need exists for bubble tubs improved relative to these deficiencies.

SUMMARY OF THE INVENTION

The invention provides an improved air delivery system for an air bath and an air bath incorporating the improved air delivery system. With the present invention, an enhanced bathing experience is achieved through a wider range of bubble densities.

Specifically, the air delivery system includes a blower generating air flow, a bypass vent in communication with ambient air, and conduit extending between the blower and the air outlets and communicating at least a portion of the air flow to the bypass vent.

In preferred forms, the bypass vent is an opening in the conduit between the blower and the air jets, for example at a T-section located in a back flow preventing loop just downstream from the blower. The back flow preventing loop, which extends vertically up to a height at or above a fill height of the basin, and a check valve, such as a spring ball check valve, in line with the conduit prevent water from backing up into the blower. The check valve and bypass vent can be located in any suitable location in line with the air flow upstream from the blower. For example, the bypass valve can be located upstream from the check valve or between the check valve and the air outlets. In any case, both the bypass vent and the check valve are preferably located at or near the back flow preventing loop.

The bypass vent preferably stays open to ambient air, and thus no valving is necessary. The flow volume through the opening is selected to ensure that during normal operation a (preferably greater) portion of the blower air flow passes to the air outlets and a (preferably lesser) portion of the air flow passes through the bypass vent. This proportion is affected by the sectional area of the opening relative to that of the conduit.

In a preferred case, the sectional area of the opening is less than one half that of the conduit, and more preferably is between 10 and 40 percent of the sectional area of the conduit. The size of the vent opening can thus be selected to create a desired bubbling effect in the basin water. By bypassing more or less air from the air outlets, there is correspondingly more or less bubbling in the basin water in terms of both the quantity and flow rate of the bubbles.

The bypass vent also plays a vital role in protecting the blower from overheating, particularly when operating a lower speeds. Since the bypass valve is open to ambient air, if the back pressure from the water head in the basin is too high for positive air flow through the air outlets, all of the air from the blower can be redirected out of the bypass valve. Since the air in this case will be passing through a smaller passage than during normal operation, there will be somewhat more back pressure on the blower, albeit not enough to cause the blower to stall, or otherwise overheat and damage the blower. As mentioned, the problem with the water pressure head blocking flow through the air outlets is most likely to arise at a low flow volume/rate, especially when the water in the basin is high. With the bypass valve, the blower can operate at low speed without stalling or overheating. As mentioned above, this gives the user a wider range of bubbling effects, particularly more subtle, softer feeling bubbles.

In addition to protecting the blower, the bypass vent also reduces or prevents chattering of the check valve that can occur in closed systems when the back pressure is about equal to the pressure from the blower. By relieving back pressure, the check valve is quieted.

In other preferred forms, a filter, such as one or more mesh screens, can be used to cover the opening and break up the exiting air flow to lessen noise. The filter may diminish flow volume through the bypass vent somewhat, and thus should be considered when sizing the vent opening. An air manifold can be provided to couple the conduit to the air outlets. The air manifold can be one or more channels extending around, and possibly integral with, the side walls of the basin.

Moreover, an electronic control and control interface can allow the user to quickly and easily adjust the air to one or more zones (feet, back, shoulders, etc.) by the press of a button. The control can also be used to control the speed of the blower to adjust the air flow rate through the manifold, and thus the density and force of bubbles in the water.

Another aspect of the invention is an air bath having an improved air delivery system. The air bath includes the basin having a bottom and side walls and the air delivery system, which includes the blower, a plurality of air outlets extending through the side walls in spaced relation, conduit extending between the blower and the air outlets, and a bypass opening in the conduit in communication with ambient air for maintaining the blower in communication with the ambient air during operation.

The above and other advantages of the invention will be apparent from the detailed description and drawings.

DETAILED DESCRIPTION OF THE PREFERRED EMBODIMENT

Figure 1:
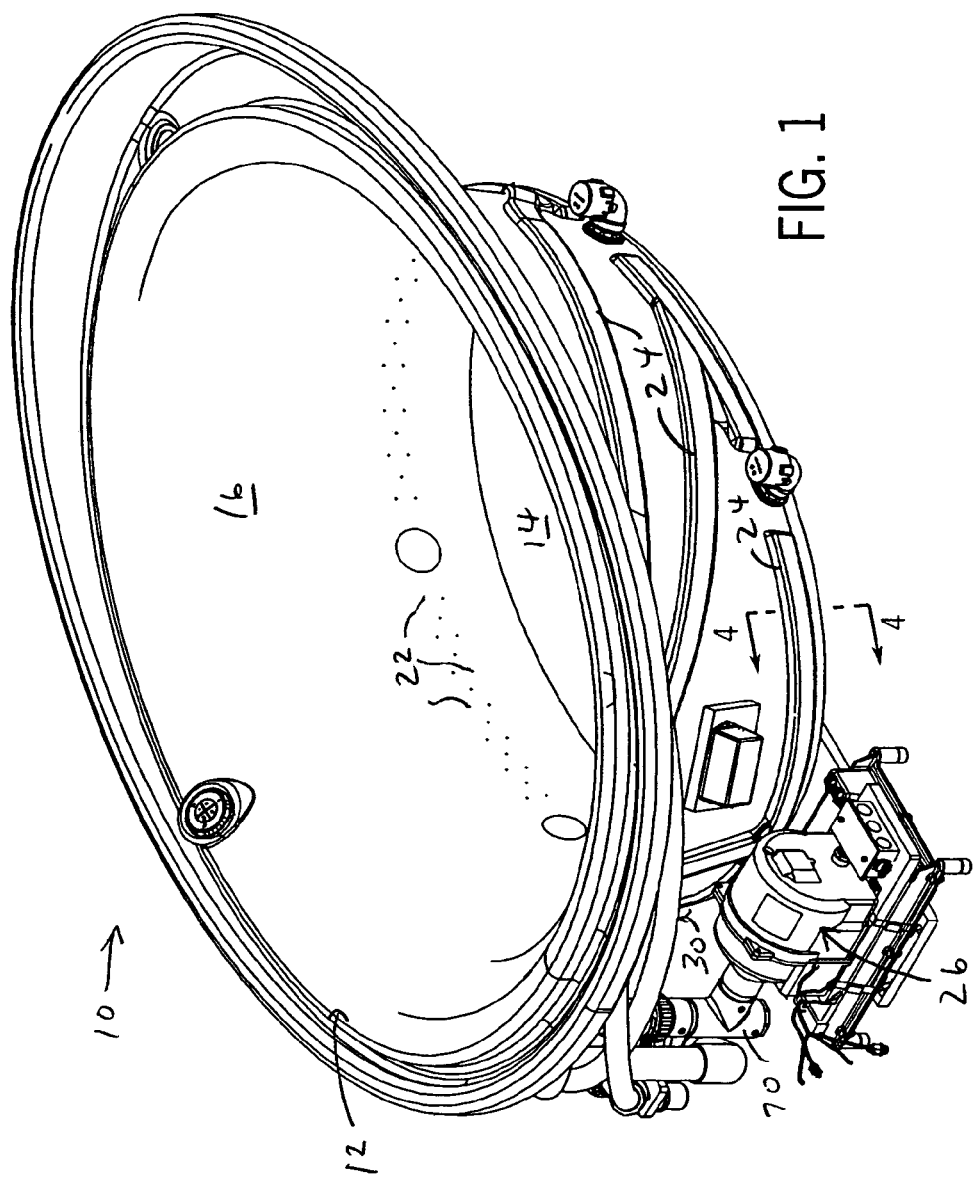
FIG. 1 is a perspective view of an air bath according to the present invention.

Referring to FIG. 1, an air bath 10 has a basin 12 defining a bottom 14 and contoured upright side walls 16. The bottom 14 has a drain opening with a drain stop controlled preferably remotely by an actuator having an overflow feature. It should be noted that while shown and described as a bathtub, the air bath 10 could be in other forms, such as a spa or swimming pool.

The side walls 16 of the basin 12 are formed with a plurality of openings defining air outlets 22, preferably in the lower half of the side walls 16. The air outlets 22 are simple round holes extending though the thickness of the side walls 16. The air outlets 22 are preferably sized and arranged in a special pattern designed to provide improved air flow for full body air induced hydrotherapy, as disclosed in the co-owned and co-pending U.S. patent application Ser. No. 10/774,123, filed on Feb. 6, 2004.

Figure 4:
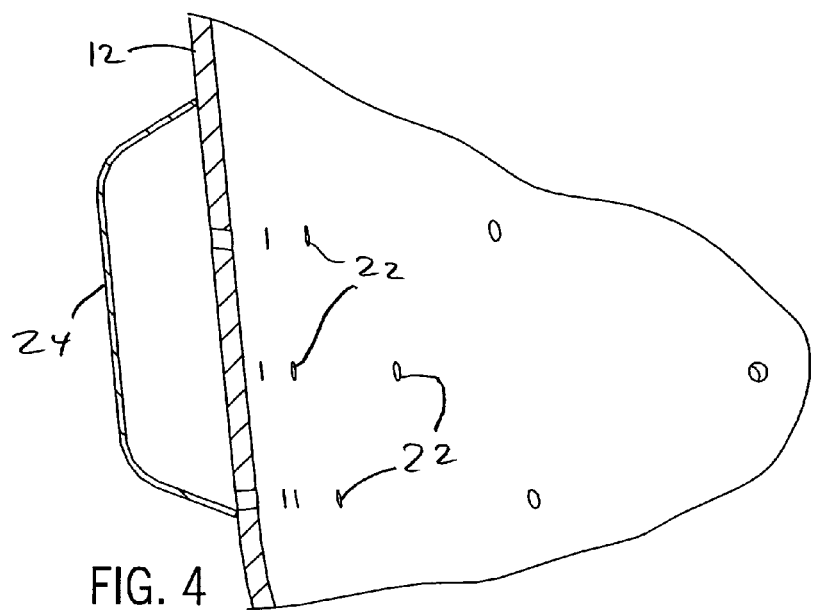
FIG. 4 is an enlarged partial sectional view taken along line 4-4 of FIG. 1 showing air outlets in the side walls of the basin.

Briefly, the air outlets 22 are arranged in a plurality of lateral (or horizontal) rows, three are shown in FIGS. 1 and 4, that essentially ring the entire perimeter of the side walls 16. If air outlets in lower rows become blocked by water pressure head being greater than the force of air exiting the associated air outlets, air may still flow from air outlets in one or more of the higher rows because of the decreased pressure head. Since the rows essentially ring the basin 12, full body treatment is achieved and maintained without unintended "dead spots" in the water (where little or no air flow occurs), which is particularly a problem when air flow is decreased for softer bubbling.

Preferably, the air outlets 22 are all in communication with an air manifold 24, which can be a single channel that rings the entire outer side perimeter of the side walls 16, or which can be a series of discrete channels (as shown in FIG. 1) that are in communication with groups of air outlets corresponding to different treatment zones. In either case, the air manifold 24 can be a separate channel (or channels) mechanically attached and sealed to the basin 12, or more preferably it can be a unitary part of the cast or molded basin 12.

Figure 2:
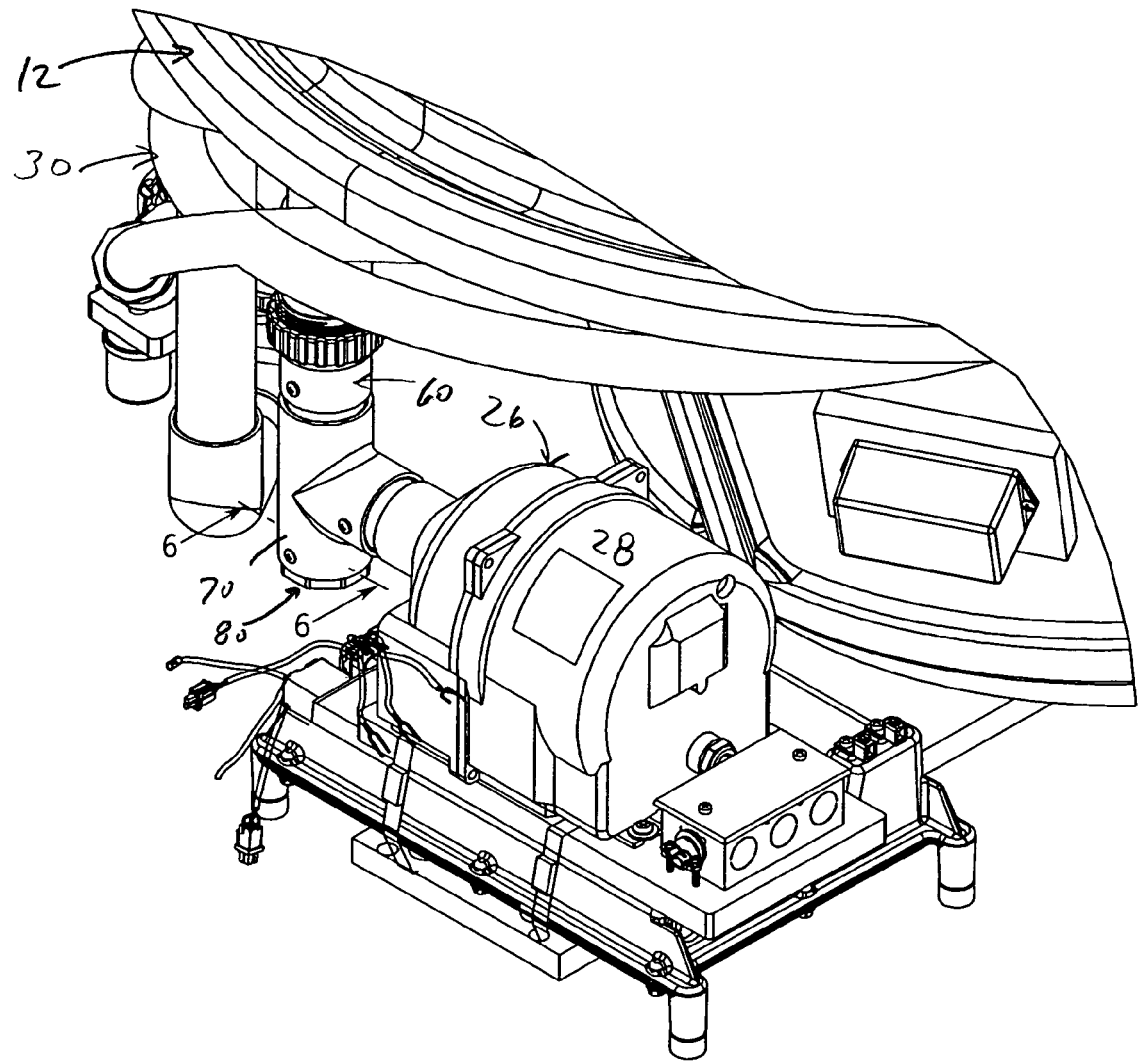
FIG. 2 is an enlarged partial perspective view showing components of the air delivery system.
Figure 3:
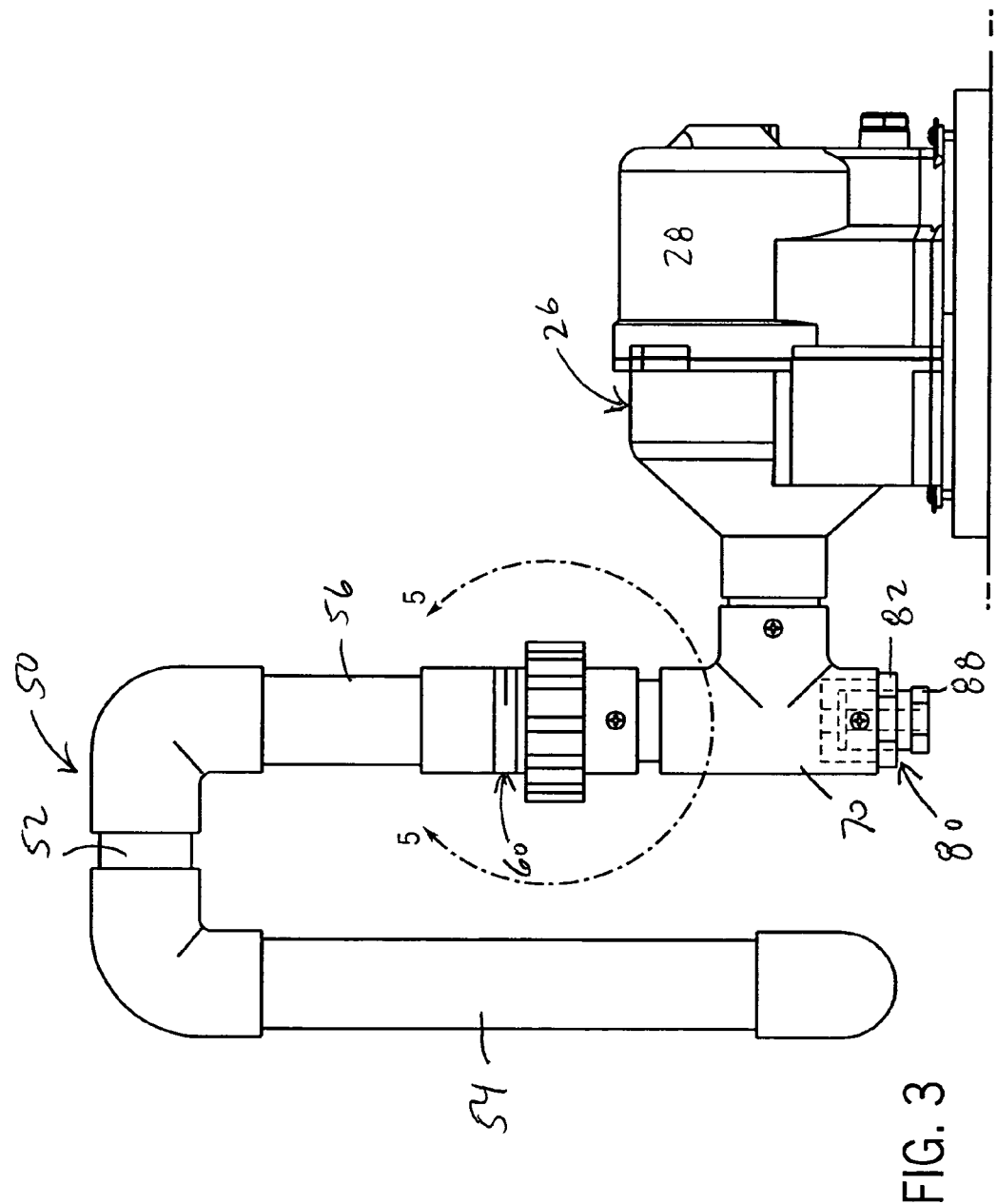
FIG. 3 is plan view thereof.
Figure 7:
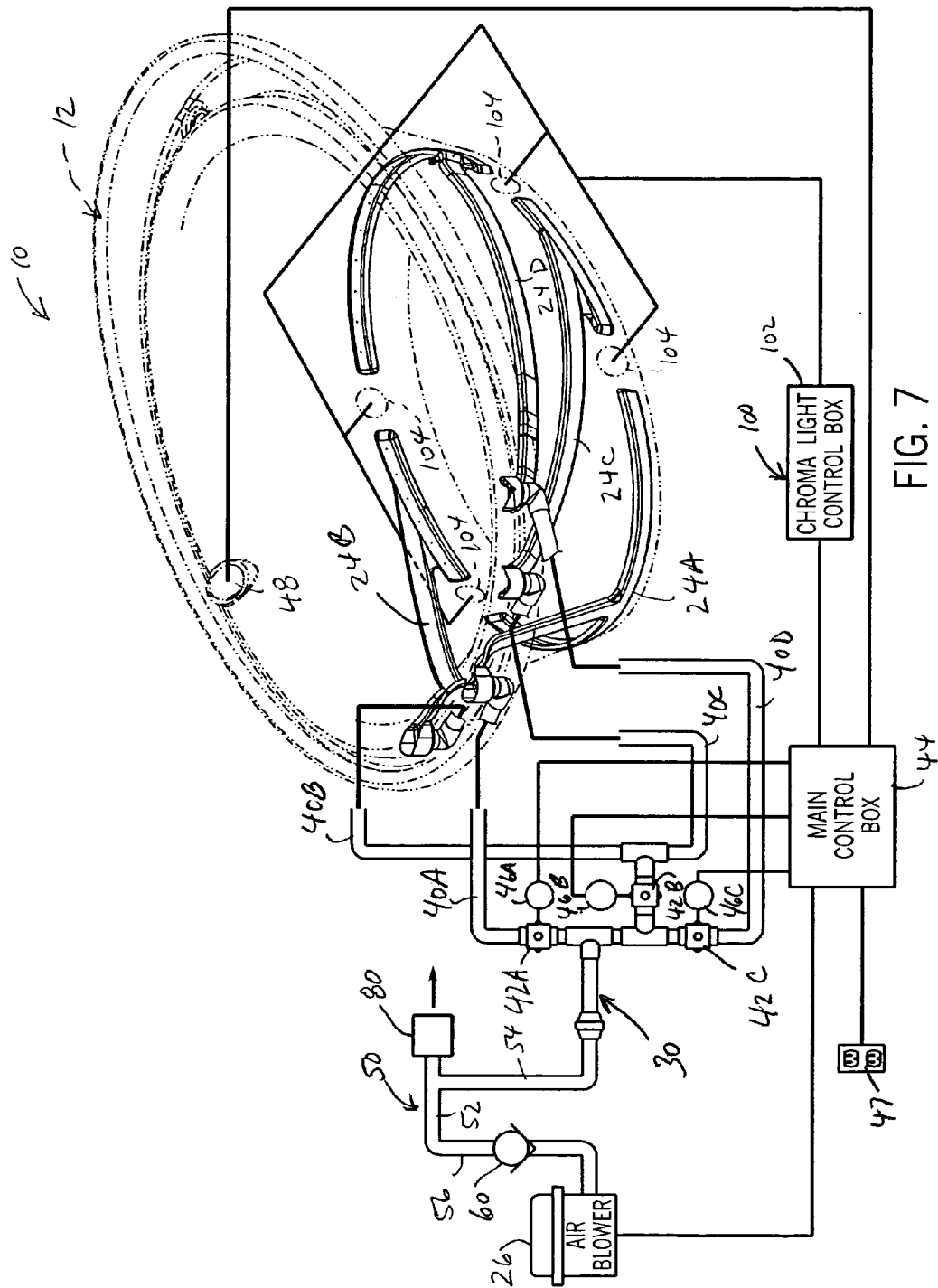
FIG. 7 illustrates schematically the vented air delivery system providing multiple air treatment zones that can be independently controlled.

With reference to FIGS. 2, 3 and 7, the air bath 10 has an air delivery system for infusing the bath water with air through the air outlets 22. Air is generated by an air pump or blower 26. The blower 26 is preferably operable at different speeds, and includes a multiple or variable speed motor 28.

The air flow is routed to the air outlets 22 by air lines or conduit 30 coupling an outlet 32 of the blower 26 to the air manifold 24. The conduit 30 can be any suitable rigid or flexible plumbing lines, however, preferably PVC tubing with a standard inner diameter is used. As is conventional, various lengths of the PVC tubing is assembled with straight or angled couplers to create the desired routing pathway.

As shown in FIGS. 1 and 7, the air delivery system includes conduit air lines (40A, 40B, 40C and 40D) for each of the channels (24A, 24B, 24C and 24D) of the air manifold 24. Air flow through air line 40A and channel 24A is controlled by a butterfly valve 42A. Air flow through both air lines 40B and 40C and respective channels 24B and 24C is controlled by a single butterfly valve 42B. Air flow through air line 40D and channel 24D is controlled by butterfly valve 42C. All of the valves are independently controllable by the controller 44 and electronically actuated actuators 46A-46C connected to the controller 44 (which is connected to power supply 47). A user control 48 for this system can have a touch pad or other button for the bather to select the zone to supply air to, which signals the controller 44 to open or close one or more of the valves 42A-42C. A full-body selection can also be provided on the user control for simultaneously opening all three valves 42A-42C.

As shown in FIGS. 2 and 3, the conduit 28 also forms a water back flow preventing loop 50 near the blower 26, generally in an inverted U-shape, a horizontal leg 52 of which is located at, or above, the maximum fill level of the basin 12, which generally is at the height of the overflow. Should water back up from the basin into the conduit, the column of water in the downstream vertical leg 54 of the loop 50 should not normally rise high enough to pass through the horizontal leg 52 and down the upstream vertical leg 56 of the loop 50.

Figure 5:
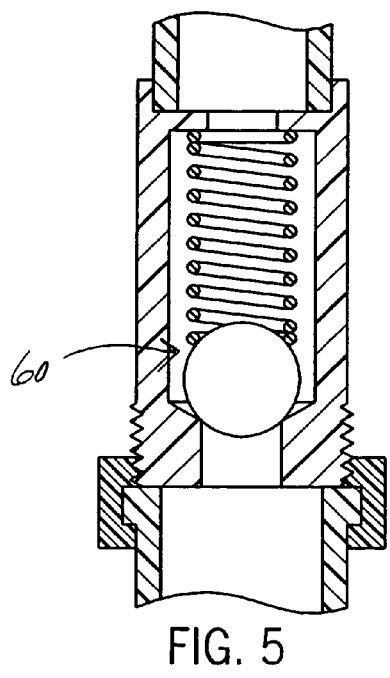
FIG. 5 is a partial sectional view taken along arc 5-5 of FIG. 3 showing a check valve.

In addition, a normally closed, spring-biased ball check valve 60 is disposed in line with the upstream vertical leg 56 to positively close off back flow to the blower 26, as shown in FIG. 5. It should be noted that in this vented system, the check valve 60 is less likely to "chatter", or oscillated rapidly between seated and unseated positions, which can occur in closed systems when the back pressure is about equal to the pressure from the blower. The check valve 60 here thus operates quietly.

Figure 6:
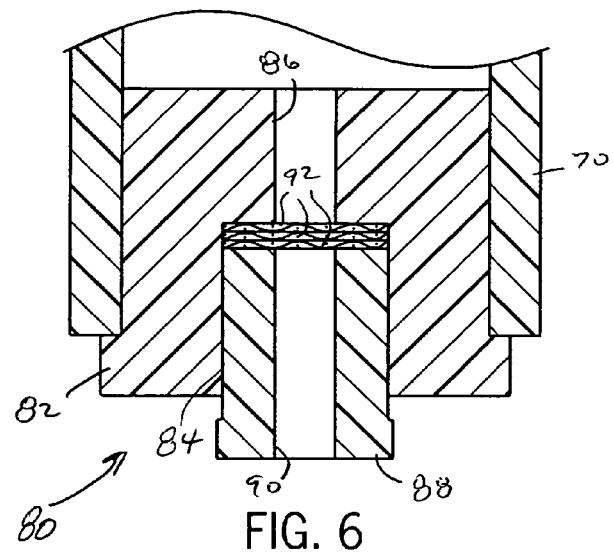
FIG. 6 is a partial sectional view taken along line 6-6 of FIG. 2 showing a bypass vent.

Referring to FIGS. 2, 3 and 6, at the junction between the outlet of the blower 26 and the upstream vertical leg 56 of the loop 50 is a T-shaped coupler 70 with a lower end not coupled to a leg of the loop 50. This end forms a bypass vent 80. More specifically, a short section 82 of conduit defining a cylindrical recess 84 at concentric with a small diameter cylindrical opening 86. A plug 88, also having a small diameter cylindrical opening 90, fits (and is secured by adhesive) into the recess 84 of the short section 82 to capture one or more mesh screens 92 therebetween so that they cover the opening 86 and cut down on noise. Instead of screens, foam pieces or other sound deadening materials may be used, as could any other suitable breathable filter elements.

The opening 86 (along with opening 90) thus forms the bypass vent 80 in that it opens the conduit 30, and thereby the blower 26, to ambient air. The bypass vent 80 must create enough back pressure so that under normal operating conditions some, in fact most, of the air flow passes onto the air outlets 22 and into the water, which creates its own back pressure. The primary way of achieving this is by sizing the opening 86 smaller than the inner diameter of the conduit 30 so that only a portion of the air flow from the blower 26 exits through the opening 86 during normal operation.

In a preferred case, the sectional area of the opening 86 is less than one half the sectional area of the conduit 30, and more preferably is between 10 and 40 percent of the sectional area of the conduit 30. Still more preferably, the opening is circular in cross-section and has a diameter less than 1 inch, for example ⅜ to ½ inch or even smaller. The inner diameter of the conduit 30 is preferably less than 3 inches, for example 1.5 or 2 inches. The air jet openings are preferably less than ¼ inch in diameter. The size of the opening 86 can thus be varied as needed for the flow requirements of a particular application and selected to create a desired bubbling effect in the basin water. By bypassing more or less air from the air outlets, there is correspondingly more or less bubbling in the basin water in terms of both the quantity and flow rate of the bubbles.

Should the back pressure from the pressure head of the water be great enough to essentially block all of the air outlets 22, the air flow in the conduit 30 will build up somewhat until it overcomes the back pressure of the bypass vent 80 and begin flowing through the opening 86 (and opening 90). While operating against slightly higher back pressure, the blower 26 can continue to operate without heating excessively or stalling. After the back pressure at the air outlets 22 has diminished sufficiently, the air flow through the conduit will resume its normal routing, with most of the air passing on to and through the air outlets 22.

As shown in FIG. 7, the bather can operate the user control 48 mounted on or near the basin 12 to operate a controller 44 to turn on and off the blower 26 as well as to adjust the bubbling effect by changing the motor speed of the blower 26. As discussed, the bypass vent allows the user to operate the blower at lower speeds for a softer, more subtle bubbling without the associated risk of damaging the blower motor otherwise present in other systems.

Finally, to further enhance the bathing experience, the air bath 10 can include a chromatherapy system 100 (including light box 102 and lights 104 mounted to the side walls) to illuminate the bath water various colors. Suitable chromatherapy systems are disclosed in U.S. Pat. Nos. 6,360,380 and 6,752,517, both of which are owned by the assignee of the present invention and incorporated by reference in their entirety as though fully set forth herein. The user control 48 and controller 44 can also be used to operate the chromatherapy system 100.

A preferred embodiment of the invention has been described in detail. However, the invention may be applied in a variety of other embodiments which are within the scope of the invention. Thus, to ascertain the full scope of the invention, the following claims should be referenced.

INDUSTRIAL APPLICABILITY

The invention provides a vented delivery system for bringing air to air outlets in bathtubs and the like.

What is claimed is:

1. An air delivery system for an air bath having a basin with side walls having a plurality of air outlets, the air delivery system comprising:
    a blower generating air flow;
    a conduit extending between the blower and the air outlets having a valve therein for controlling air flow to the air outlets; and
    a bypass vent coupled to the conduit downstream from the blower and upstream from the valve in the conduit, wherein the bypass vent is an opening in a section of the conduit such that the blower is maintained in communication with ambient air via the bypass vent and wherein the opening is of a lesser sectional area than that of the conduit so as to create back pressure in the conduit such that at least a portion of the air from the blower flows to the air outlets at least until a threshold water head pressure is reached within the basin.

2. The air delivery system of claim 1, wherein the sectional area of the opening is less than one half the sectional area of the conduit.

3. The air delivery system of claim 2, wherein the sectional area of the opening is between 10 and 40 percent of the sectional area of the conduit.

4. The air delivery system of claim 1, wherein the opening has a diameter less than ½ inch.

5. The air delivery system of claim 1, further including a filter covering the opening.

6. The air delivery system of claim 5, wherein the filter includes at least one mesh screen.

7. The air delivery system of claim 1, wherein the conduit in part forms a backflow preventing loop having a section of conduit at a height at or above a fill height of the basin.

8. The air delivery system of claim 7, wherein the bypass vent is located along the backflow preventing loop.

9. The air delivery system of claim 1, further including a check valve in line with the conduit downstream from an outlet of the blower.

10. The air delivery system of claim 9, wherein the bypass vent is disposed in the conduit upstream from the check valve.

11. The air delivery system of claim 9, wherein the bypass vent is formed in a T-section of the conduit.

12. The air delivery system of claim 1, further including an air manifold coupling the conduit to the air outlets.

13. The air delivery system of claim 12, wherein the air manifold includes one or more channels extending around the side walls of the basin.

14. The air delivery system of claim 13, wherein the air manifold is integral with an outer side of the side walls of the basin.

15. The air delivery system of claim 1, wherein the air outlets are arranged in vertically spaced rows located vertically within a lower half of the side walls of the basin.

16. The air delivery system of claim 1, wherein the blower is variable speed.

17. An air bath, comprising:
a basin having a bottom and side walls;
an air delivery system including:
a blower;
a plurality of air outlets extending through the side walls in spaced relation;
a conduit extending between the blower and the air outlets having at least one valve therein for controlling air flow to the air outlets; and
a bypass opening in the conduit downstream from the blower and upstream from the at least one valve in communication with ambient air for maintaining the blower in communication with the ambient air during operation, wherein the bypass opening is maintained in communication with ambient air during operation and wherein the opening is of a lesser sectional area than that of the conduit so as to create back pressure in the conduit such that at least a portion of the air from the blower flows to the air outlets at least until a threshold water head pressure is reached within the basin.

\* \* \* \* \*

UNITED STATES PATENT AND TRADEMARK OFFICE
CERTIFICATE OF CORRECTION

PATENT NO. : 7,614,095 B2 Page 1 of 1
APPLICATION NO. : 10/867539
DATED : November 10, 2009
INVENTOR(S) : Swart et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this

Nineteenth Day of October, 2010

David J. Kappos
*Director of the United States Patent and Trademark Office*